(12) United States Patent
Parthasaradhi Reddy et al.

(10) Patent No.: US 9,175,005 B2
(45) Date of Patent: Nov. 3, 2015

(54) CRYSTALLINE HYDROCHLORIDE SALT OF DARUNAVIR

(71) Applicant: HETERO RESEARCH FOUNDATION, Andhrapradesh (IN)

(72) Inventors: Bandi Parthasaradhi Reddy, Andhrapradesh (IN); Kura Rathnakar Reddy, Andhrapradesh (IN); Dasari Muralidhara Reddy, Andhrapradesh (IN); Rapolu Raji Reddy, Andhrapradesh (IN); Bandi Vamsi Krishna, Andhrapradesh (IN); Kesireddy Subash Chander Reddy, Andhrapradesh (IN)

(73) Assignee: HETERO RESEARCH FOUNDATION (IN)

( * ) Notice: Subject to any disclaimer, the term of this patent is extended or adjusted under 35 U.S.C. 154(b) by 0 days.

(21) Appl. No.: 14/325,869

(22) Filed: Jul. 8, 2014

(65) Prior Publication Data
US 2015/0080589 A1   Mar. 19, 2015

Related U.S. Application Data

(62) Division of application No. 13/699,096, filed as application No. PCT/IN2010/000339 on May 20, 2010, now Pat. No. 8,853,430.

(51) Int. Cl.
C07D 493/04 (2006.01)
C07D 307/93 (2006.01)

(52) U.S. Cl.
CPC ............ *C07D 493/04* (2013.01); *C07D 307/93* (2013.01)

(58) Field of Classification Search
CPC ........................... C07D 307/93; C07D 493/04
See application file for complete search history.

(56) References Cited

U.S. PATENT DOCUMENTS

| | | | |
|---|---|---|---|
| 3,876,632 A | 4/1975 | Sturm et al. | |
| 4,670,578 A | 6/1987 | Budavari et al. | |
| 4,692,438 A | 9/1987 | Hassall et al. | |
| 5,315,016 A | 5/1994 | Hansen et al. | |
| 6,248,775 B1 * | 6/2001 | Vazquez et al. | 514/445 |
| 7,649,010 B2 | 1/2010 | Chen et al. | |
| 7,700,645 B2 | 4/2010 | Vermeersch et al. | |
| 8,921,415 B2 * | 12/2014 | Marom | 514/465 |
| 2003/0125336 A1 | 7/2003 | Fleitz et al. | |
| 2005/0250845 A1 | 11/2005 | Vermeersch et al. | |
| 2008/0269322 A1 | 10/2008 | De Kock et al. | |
| 2009/0111796 A1 | 4/2009 | Muto et al. | |
| 2010/0094028 A1 | 4/2010 | Lemaire et al. | |
| 2011/0313035 A1 | 12/2011 | Reddy et al. | |
| 2012/0088808 A1 | 4/2012 | Pichler et al. | |
| 2012/0288563 A1 | 11/2012 | Reddy et al. | |
| 2013/0072552 A1 | 3/2013 | Parthasaradhi Reddy et al. | |

FOREIGN PATENT DOCUMENTS

| | | |
|---|---|---|
| EP | 0715618 B1 | 12/1998 |
| WO | 9967417 A1 | 12/1999 |
| WO | 03106461 A1 | 12/2003 |
| WO | 2006067795 A2 | 6/2006 |
| WO | 2007054969 A2 | 5/2007 |
| WO | 2010086844 A1 | 8/2010 |
| WO | 2011073993 A1 | 6/2011 |

OTHER PUBLICATIONS

Van Gysegham et al. in European Journal of Pharmaceutical Sciences 38 (2009) 489-497.*
U.S. Appl. No. 13/128,157, filed Jul. 6, 2011; Final Office Action; Mailed Oct. 22, 2013.
U.S. Appl. No. 13/128,157, filed Jul. 6, 2011; Final Office Action of Oct. 22, 2013.
U.S. Appl. No. 13/530,844, filed Jun. 22, 2012; Final Office Action; Mailed May 20, 2014; 20 pages.
U.S. Appl. No. 13/530,844, filed Jun. 22, 2012; final Office Action Mailed May 20, 2014; 20 pages.
U.S. Appl. No. 13/530,844, filed Jun. 22, 2012; NonFinal Office Action of Jan. 7, 2014; 31 pages.
U.S. Appl. No. 14/047,243, filed Oct. 7, 2013.
Bastin et al. in Organic Process & Development 4, pp. 427-435; (2000).
Chemist's Companion, A. J. gordon and R. A. Ford, Wiley-Interscience, 1972.
Ghosh et al.; "Potent HIV Protease Inhibitors Incorporating High-Affinity P2-Ligands and (R)-(Hydroxyethylamino) Sulfonamide Isostere"; Bioorganic & Medicinal Chemistry Letters; 8; pp. 687-690; (1998).
Morissette et al.; in Advance Drug Delivery Reviews; 56; pp. 275-300; (2004).
International Search Report; International Application No. PCT/IN2009/000724; International Filing Date Dec. 16, 2009; Date of Mailing Jan. 3, 2011; 4 pages.
International Search Report and Written Opinion; International Application No. PCT/IN2010/000339; International Filing Date May 20, 2010; Date of Mailing Jan. 6, 2011; 12 Pages.

(Continued)

*Primary Examiner* — Dennis Heyer
(74) *Attorney, Agent, or Firm* — Cantor Colburn LLP

(57) ABSTRACT

The present invention provides novel crystalline hydrochloride salt of darunavir, process for its preparation and to pharmaceutical composition comprising it. The present invention also provides novel process for preparation of darunavir amorphous form and pharmaceutical composition comprising it.

11 Claims, 2 Drawing Sheets

(56) References Cited

OTHER PUBLICATIONS

Potent HIV Protease . . . Bioorganic & Medicinal Chemistry Letters; 8; pp. 687-690; (1998).

Vippagunta et al.; "Crystalline Solids"; Advanced Drug Delivery Reviews; 48; pp. 3-26; (2001).
Yu, Lian; "Amorophous Pharmaceutical Solids: Preparation, Characterization and Stabilization"; Advanced Drug Delivery Reviews; 48; pp. 27-42; (2001).

\* cited by examiner

CRYSTALLINE HYDROCHLORIDE SALT OF DARUNAVIR

CROSS-REFERENCE TO RELATED APPLICATIONS

This application is a divisional of U.S. application Ser. No. 13/699,096, filed on Feb. 7, 2013, which is a 371 of PCT/IN2010/000339 filed May 20, 2010, under the provisions of 35 U.S.C. 119 and the International Convention for the protection of Industrial Property, which are incorporated herein by reference.

FIELD OF THE INVENTION

The present invention provides novel crystalline hydrochloride salt of darunavir, process for its preparation and to pharmaceutical composition comprising it. The present invention also provides novel process for preparation of darunavir amorphous form and pharmaceutical composition comprising it.

BACKGROUND OF THE INVENTION

Virus-encoded proteases, which are essential for viral replication, are required for the processing of viral protein precursors. Interference with the processing of protein precursors inhibits the formation of infectious virions. Accordingly, inhibitors of viral proteases may be used to prevent or treat chronic and acute viral infections. Darunavir has HIV protease inhibitory activity and is particularly well suited for inhibiting HIV-1 and HIV-2 viruses. Among them darunavir, chemically (1S,2R,3'R,3'aS,6'aR)-[3'-hexahydrofuro[2,3-b]furanyl-[3-(4-aminobenzenesulfonyl)isobutylamino]-1-benzyl-2-hydroxypropyl]carbamate. Darunavir is represented by the following structure:

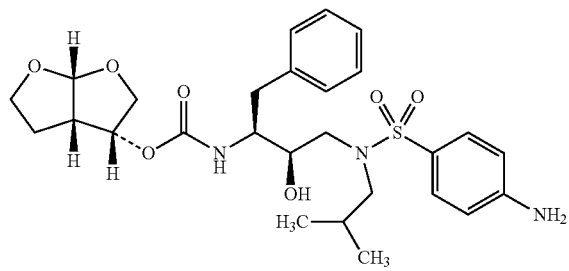 [SMILES: CC(C)CN(C[C@@H](O)[C@H](Cc1ccccc1)NC(=O)O[C@H]1CO[C@H]2OCC[C@H]21)S(=O)(=O)c1ccc(N)cc1]

Darunavir and its pharmaceutical acceptable salts such as hydrochloride were described in EP 715618.

Processes for the preparations of darunavir were disclosed in EP 715618, WO 99/67417, U.S. Pat. No. 6,248,775, and in Bioorganic and Chemistry Letters, Vol. 8, pp. 687-690, 1998, "Potent HIV protease inhibitors incorporating high-affinity P2-igands and (R)-(hydroxyethylamino)sulfonamide isostere", all of which are incorporated herein by reference.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Darunavir or its hydrochloride salt can exist in different polymorphic forms, which may differ from each other in terms of stability, physical properties, spectral data and methods of preparation.

U.S. Patent Application No. 2005/0250845 described amorphous form, form A (ethanolate), form B (hydrate), form C (methanolate), form D (acetonate), form E (dichloromethanate), form F (ethylacetate solvate), form G (1-ethoxy-2-propanolate), form H (anisolate), form I (tetrahydrofuranate), form J (isopropanolate) and form K (mesylate) of darunavir.

Darunavir $C_5$-$C_8$ alcohol solvate and process for its preparation was disclosed in co-pending Application No. PCT/IN2009/000724. According to the application also disclosed a process for the preparation of darunavir amorphous form which comprises a solution of darunavir $C_5$-$C_8$ alcohol solvate in dichloromethane, removing the solvent from the solution to obtain a residue, slurrying the residue with cyclohexane and isolating.

We have discovered novel crystalline hydrochloride salt of darunavir and also discovered novel process for the preparation of darunavir amorphous form.

Thus, one object of the present invention is to provide novel crystalline hydrochloride salt of darunavir, process for its preparation and to pharmaceutical compositions comprising it.

The salt of the present invention may also serve as intermediates for preparation of darunavir amorphous form and other polymorphs of darunavir.

Another object of the present invention is to provide a novel process for preparation of darunavir amorphous form and pharmaceutical compositions comprising it.

SUMMARY OF THE INVENTION

In one aspect, the present invention provides a crystalline hydrochloride salt of darunavir.

In another aspect, the present invention provides a process for the preparation of crystalline hydrochloride salt of darunavir, which comprises:
    a) providing a solution of darunavir in a solvent;
    b) adding hydrochloric acid to the solution obtained in step (a);
    c) slurrying the reaction mass obtained in step (b) at below 40° C.; and
    d) isolating crystalline hydrochloride salt of darunavir.

In another aspect, the present invention provides a pharmaceutical composition comprising crystalline hydrochloride salt of darunavir and a pharmaceutically acceptable excipient.

In another aspect, the present invention provides a process for the preparation of darunavir amorphous form, which comprises:
    a) dissolving darunavir or pharmaceutical acceptable salts in a solvent and water;

b) adjusting the pH of the reaction mass to about 7.0 to 8.5 with a base;
c) removing the solvent from the solution obtained in step (b) to obtain a residual mass;
d) slurrying the residual mass obtained in step (b) with aliphatic hydrocarbon solvent or aromatic solvent; and
e) isolating darunavir amorphous form.

In yet another aspect, the present invention provides a pharmaceutical composition comprising darunavir amorphous form and a pharmaceutically acceptable excipient.

X-ray powder diffraction spectrum was measured on a bruker axs D8 advance X-ray powder diffractometer having a copper-K$\alpha$ radiation. Approximately 1 gm of sample was gently flattered on a sample holder and scanned from 2 to 50 degrees two-theta, at 0.02 degrees to theta per step and a step of 10.4 seconds. The sample was simply placed on the sample holder. The sample was rotated at 30 rpm at a voltage 40 KV and current 35 mA.

DETAILED DESCRIPTION OF THE INVENTION

According to one aspect of the present invention, there is provided a crystalline hydrochloride salt of darunavir.

Figure 1:
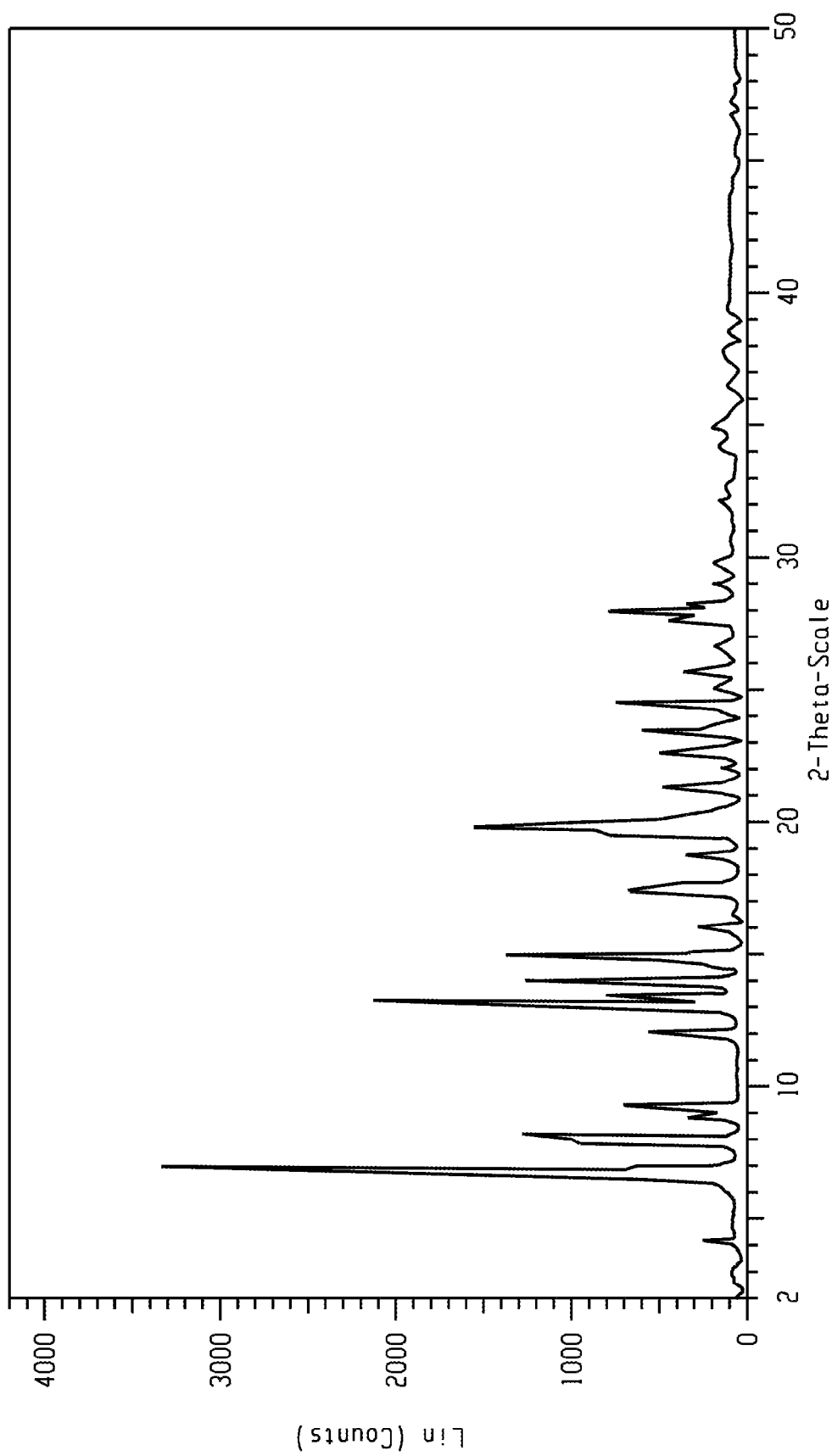
FIG. 1 is X-ray powder diffraction spectrum of crystalline hydrochloride salt of darunavir.
Figure 2:
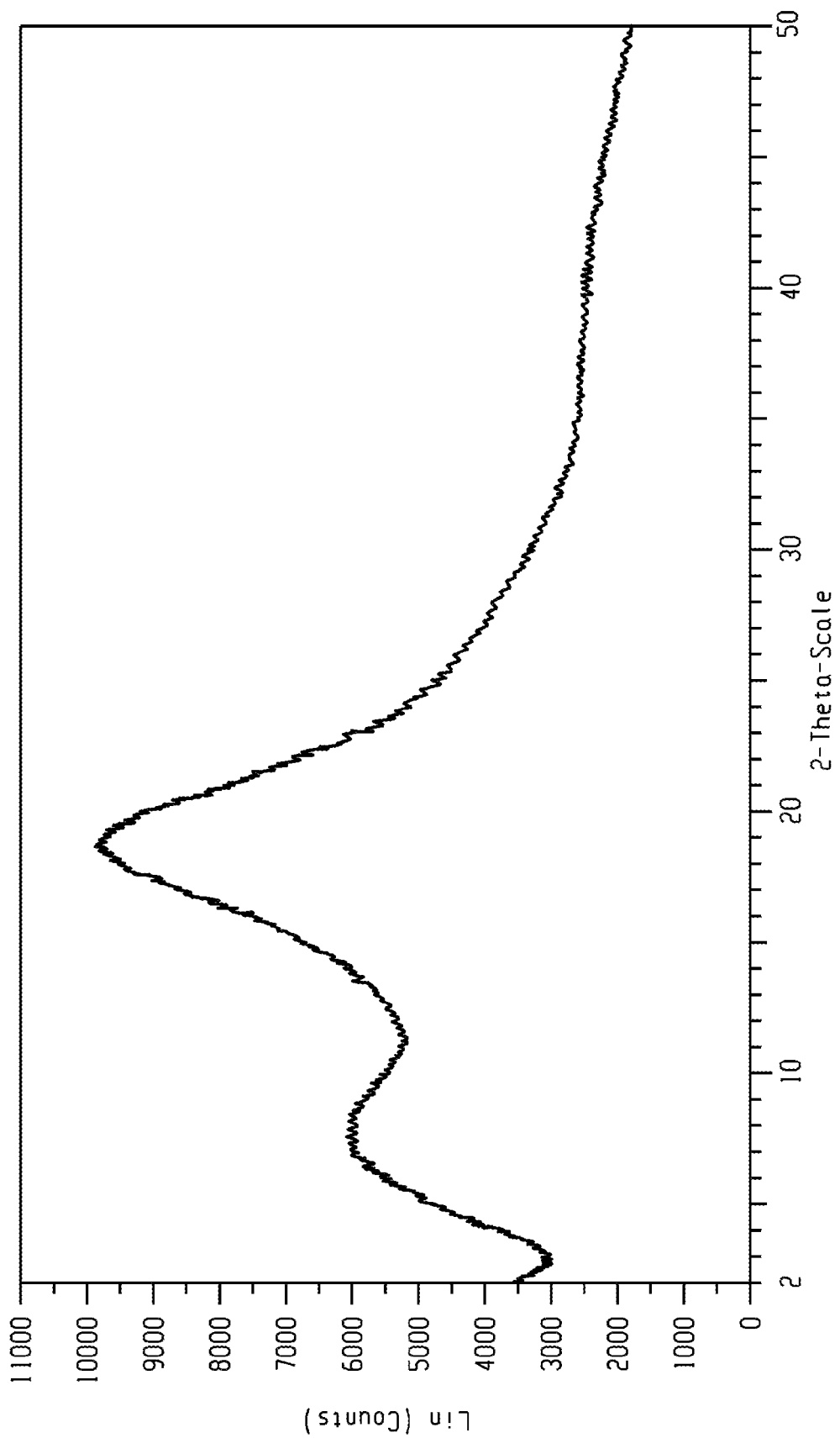
FIG. 2 is X-ray powder diffraction spectrum of darunavir amorphous form.

Crystalline hydrochloride salt of darunavir which is characterized by peaks in the powder x-ray diffraction spectrum having 2θ angle positions at about 6.7, 8.0, 13.1, 13.9, 14.9, 19.6, 19.9, 24.5 and 27.9±0.2 degrees. The powdered x-ray diffractogram (PXRD) of crystalline hydrochloride salt of darunavir is shown in FIG. 1.

According to another aspect of the present invention, there is provided a process for the preparation of crystalline hydrochloride salt of darunavir, which comprises:
a) providing a solution of darunavir in a solvent;
b) adding hydrochloric acid to the solution obtained in step (a);
c) slurrying the reaction mass obtained in step (b) at below 40° C.; and
d) isolating crystalline hydrochloride salt of darunavir.

The solvent used in step (a) may preferably be a solvent or mixture of solvents selected from the group consisting of water; a halogenated hydrocarbon solvents such as dichloromethane, chloroform, carbontetrachloride and ethylene dichloride; an ester solvents such as ethyl acetate, methyl acetate, isopropyl acetate, tert-butyl methyl acetate and ethyl formate; a ketonic solvents such as acetone, methyl ethyl ketone, methyl isobutyl ketone and diethyl ketone; an ether solvents such as tetrahydrofuran, 1,4-dioxane, methyl tert-butyl ether, diisopropyl ether and diethyl ether. More preferable solvent is water, dichloromethane, ethyl acetate, methyl isobutyl ketone, methyl tert-butyl ether and diisopropyl ether.

Darunavir used in step (a) may be darunavir in any solvated or hydrated or anhydrous form and preferably the darunavir is darunavir $C_5$-$C_8$ alcohol solvate such as 2-methyl-2-butanol solvate or n-pentanol solvate, darunavir ethanolate and anhydrous form of darunavir.

Hydrochloric acid can be used in step (b) as an aqueous hydrochloric acid or anhydrous hydrochloric acid and preferably aqueous hydrochloric acid is used.

Preferably the slurrying may be carried out at room temperature for at least 30 minutes.

The isolation of crystalline hydrochloride salt of darunavir in step (d) may preferably be performed by conventional techniques such as centrifugation and filtration.

According to another aspect of the present invention, there is provided a pharmaceutical composition which comprises crystalline hydrochloride salt of darunavir and pharmaceutically acceptable carriers, diluents or excipients and optionally other therapeutic ingredients. The salt may preferable be conveniently formulated into tablets, capsules, suspensions, dispersions, injectables and other pharmaceutical forms.

According to another aspect of the present invention, there is provided a process for the preparation of darunavir amorphous form, which comprises:
a) dissolving darunavir or pharmaceutical acceptable salts in a solvent and water;
b) adjusting the pH of the reaction mass to about 7.0 to 8.5 with a base;
c) removing the solvent from the solution obtained in step (b) to obtain a residual mass;
d) slurrying the residual mass obtained in step (b) with aliphatic hydrocarbon solvent or aromatic solvent; and
e) isolating darunavir amorphous form.

Darunavir or its pharmaceutical acceptable salts used in step (a) is crystalline hydrochloride salt of darunavir.

The solvent used in step (a) may preferably be a solvent or mixture of solvents selected from the group consisting of a halogenated hydrocarbon solvents such as dichloromethane, chloroform, carbontetrachloride and ethylene dichloride; an ester solvents such as ethyl acetate, methyl acetate, isopropyl acetate, tert-butyl methyl acetate and ethyl formate; a ketonic solvents such as acetone, methyl ethyl ketone, methyl isobutyl ketone and diethyl ketone; an ether solvents such as tetrahydrofuran, 1,4-dioxane, methyl tert-butyl ether, diisopropyl ether and diethyl ether. More preferable solvent is dichloromethane, ethyl acetate, methyl isobutyl ketone, methyl tert-butyl ether and diisopropyl ether.

Preferably the pH of the reaction mass in step (b) may be adjusted to 7.2-8.2 and more preferably the pH adjusted to 7.5-8.0.

The base used in step (b) may preferably be an organic base or an inorganic base selected from ammonium, sodium hydroxide and potassium hydroxide, and more preferably the base is ammonia.

Removal of the solvent may be carried out in step (c) at atmospheric pressure or at reduced pressure. Removal of the solvent may preferably be carried out until the solvent is almost completely distilled off.

The aliphatic hydrocarbon solvent or aromatic solvent used in step (d) may preferably be a solvent or a mixture of solvents selected from cyclohexane, hexane, n-heptane, toluene and xylene. More preferable aliphatic hydrocarbon solvent is cyclohexane.

The isolation of darunavir amorphous form in step (e) may preferably be performed by conventional techniques such as centrifugation and filtration.

According to another aspect of the present invention, there is provided a pharmaceutical composition comprising a darunavir amorphous form and a pharmaceutically acceptable excipient.

The pharmaceutically acceptable inert carrier which can be used may be a solid dosage forms.

The solid dosage forms for oral administration may include capsules, tablets, pills, powders and granules.

The invention will now be further described by the following examples, which are illustrative rather than limiting.

EXAMPLES

Example 1

Preparation of Crystalline Hydrochloride Salt of Darunavir

To a mixture of (3R,3aS,6aR)-hexahydrofuro[2,3-b]furan-3-ol (66 gm) and acetonitrile (300 ml) was added disuccinimidyl carbonate (110 gm) at 25 to 30° C. The reaction mass was cooled to 10° C. under nitrogen atmosphere and then added pyridine (93 gm) for 30 minutes. The temperature of the reaction mass was raised to 30° C. and stirred for 1 hour 30 minutes at 30° C. The reaction mass further cooled to −10° C. under nitrogen atmosphere. A solution of 4-amino-N-((2R,3S)-3-amino-2-hydroxy-4-phenylbutyl)-N-(isobutyl)benzene sulfonamide (135 gm) in acetonitrile (330 ml) was added to the reaction mass at −10 to −15° C. for 45 minutes. To the reaction mass was added triethylamine (39 gm) and monomethylamine (5.8 gm) at −10° C., and the temperature was slowly raised to 20 to 25° C. and stirred for 1 hour. The reaction mass distilled off the solvent completely removed under vacuum at below 50° C. to obtain a residue. To the residue was added dichloromethane (1000 ml). The dichloromethane layer was washed with 10% sodium bicarbonate (500 ml), 2% sulfuric acid (500 ml), 10% sodium sulfate (500 ml) and 10% sodium chloride solution (500 ml). The layer was treated with carbon and then added concentrated hydrochloric acid (40 ml). The reaction mass was stirred for 1 hour at 25 to 30° C. and filtered. The solid obtained was dried under vacuum at 60 to 65° C. for 6 hours to obtain 140 gm of crystalline hydrochloride salt of darunavir.

Example 2

Preparation of Crystalline Hydrochloride Salt of Darunavir

Darunavir 2-methyl-2-butanol solvate (100 gm) was dissolved in dichloromethane (1000 ml) and stirred to obtain a solution. To the solution was added concentrated hydrochloric acid (30 ml) and stirred for 1 hour at 25 to 30° C. The separated solid was filtered and dried under vacuum at 60 to 65° C. for 6 hours to obtain 97 gm of crystalline hydrochloride salt of darunavir.

Example 3

Preparation of Crystalline Hydrochloride Salt of Darunavir

Darunavir n-pentanol solvate (50 gm) was dissolved in dichloromethane (500 ml) and water (50 ml) under stirring. To the solution was added concentrated hydrochloric acid (20 ml) and stirred for 1 hour at 25 to 30° C. The separated solid was filtered and dried under vacuum at 60 to 65° C. for 6 hours to obtain 45 gm of crystalline hydrochloride salt of darunavir.

Example 4

Preparation of Crystalline Hydrochloride Salt of Darunavir

Darunavir (10 gm) was dissolved in dichloromethane (100 ml) and stirred to obtain a solution. To the solution was added concentrated hydrochloric acid (3 ml) and stirred for 1 hour at 25 to 30° C. The separated solid was filtered and dried under vacuum at 60 to 65° C. for 6 hours to obtain 9.8 gm of crystalline hydrochloride salt of darunavir.

Example 5

Preparation of Crystalline Hydrochloride Salt of Darunavir

Darunavir ethanolate (100 gm) was dissolved in ethyl acetate (1000 ml) and stirred to obtain a solution. To the solution was added concentrated hydrochloric acid (30 ml) and stirred for 1 hour at 25 to 30° C. The separated solid was filtered and dried under vacuum at 60 to 65° C. for 6 hours to obtain 95 gm of crystalline hydrochloride salt of darunavir.

Example 6

Preparation of Crystalline Hydrochloride Salt of Darunavir

Example 4 was repeated using ethyl acetate solvent instead of dichloromethane solvent to obtain crystalline hydrochloride salt of darunavir.

Example 7

Preparation of Crystalline Hydrochloride Salt of Darunavir

Example 4 was repeated using methyl tert-butyl ether solvent instead of dichloromethane solvent to obtain crystalline hydrochloride salt of darunavir.

Example 8

Preparation of Crystalline Hydrochloride Salt of Darunavir

Example 4 was repeated using methyl isobutyl ketone solvent instead of dichloromethane solvent to obtain crystalline hydrochloride salt of darunavir.

Example 9

Preparation of Crystalline Hydrochloride Salt of Darunavir

Example 4 was repeated using diisopropyl ether solvent instead of dichloromethane solvent to obtain crystalline hydrochloride salt of darunavir.

Example 10

Preparation of Darunavir Amorphous Form

Crystalline hydrochloride salt of darunavir (135 gm) as obtained in example 1 was dissolved in dichloromethane (1200 ml) and water (1000 ml) at room temperature. The pH of the reaction mass was adjusted to 7.5 to 8.0 with ammonium solution and stirred for 20 minutes. The organic layer was treated with carbon and distilled off the solvent completely under vacuum at 45° C. to obtain foam like residue. Cyclohexane (1000 ml) was added to the residue, distilled off the solvent completely under vacuum at 45° C. to obtain residue. To the residue was added cyclohexane (100 ml) and stirred for 4 hours at 20 to 25° C. The separated solid was filtered and dried under vacuum at 50° C. for 12 hours to obtain 120 gm of darunavir amorphous form.

Example 11

Preparation of Darunavir Amorphous Form

Crystalline hydrochloride salt of darunavir (5 gm) was dissolved in ethyl acetate (50 ml) and water (50 ml) at room temperature. The pH of the reaction mass was adjusted to 7.5 to 8.0 with ammonium solution and stirred for 20 minutes. The organic layer was treated with carbon and distilled off the solvent under vacuum at 45° C. to obtain foam like residue. Cyclohexane (25 ml) was added to the residue, distilled off the solvent completely under vacuum at 45° C. to obtain a residue. To the residue was added cyclohexane (50 ml) and stirred for 5 hours at 25 to 30° C., filtered. The solid obtained was dried under vacuum at 50° C. for 12 hours to obtain 4.2 gm of darunavir amorphous form.

Example 12

Preparation of Darunavir Amorphous Form

Example 10 was repeated using methyl tert-butyl ether solvent instead of dichloromethane solvent to obtain darunavir amorphous form.

Example 13

Preparation of Darunavir Amorphous Form

Example 10 was repeated using methyl isobutyl ketone solvent instead of dichloromethane solvent to obtain darunavir amorphous form.

We claim:

1. A process for the preparation of darunavir amorphous form, comprising
   a. dissolving a crystalline hydrochloride salt of darunavir in an organic solvent and water to form a reaction mass;
   b. adjusting the pH of the reaction mass to about 7.0 to 8.5 with a base to form a solution;
   c. removing the organic solvent from the solution obtained in step (b) to provide a residual mass;
   d. slurrying the residual mass obtained in step (b) with an aliphatic hydrocarbon solvent or an aromatic solvent; and
   e. isolating darunavir amorphous form.

2. The process according to claim 1, wherein the organic solvent used in step (a) is a solvent or mixture of solvents selected from a halogenated hydrocarbon solvent, a ketonic solvent, an ester solvent, and an ether solvent.

3. The method of claim 2, wherein the organic solvent is dichloromethane, chloroform, carbon tetrachloride, ethylene dichloride, ethyl acetate, methyl acetate, isopropyl acetate, tert-butyl methyl acetate, ethyl formate, acetone, methyl ethyl ketone, methyl isobutyl ketone, diethyl ketone, tetrahydrofuran, 1,4-dioxane, methyl tert-butyl ether, diisopropyl ether, or diethyl ether.

4. The process according to claim 2, wherein the organic solvent is dichloromethane, ethyl acetate, methyl isobutyl ketone, methyl tert-butyl ether, or diisopropyl ether.

5. The process according to claim 1, wherein the pH of the reaction mass in step (b) is adjusted to 7.2 to 8.2.

6. The process according to claim 5, wherein the pH is adjusted to 7.5 to 8.0.

7. The process according to claim 1, wherein the base used in step (b) is ammonia, sodium hydroxide, or potassium hydroxide.

8. The process according to claim 7, wherein the base is ammonia.

9. The process according to claim 1, wherein the aliphatic hydrocarbon solvent or aromatic solvent used in step (d) is cyclohexane, hexane, n-heptane, toluene, xylene, or a mixture thereof.

10. The process according to claim 9, wherein the aliphatic hydrocarbon solvent is cyclohexane.

11. The process according to claim 1, wherein the darunavir hydrochloride salt is a crystalline hydrochloride salt of darunavir characterized by peaks in the powder x-ray diffraction spectrum having 2θ angle positions at 6.7, 8.0, 13.1, 13.9, 14.9, 19.6, 19.9, 24.5 and 27.9±0.2 degrees.

* * * * *